United States Patent [19]

Shimmick et al.

[11] Patent Number: 5,556,395
[45] Date of Patent: Sep. 17, 1996

[54] METHOD AND SYSTEM FOR LASER TREATMENT OF REFRACTIVE ERROR USING AN OFFSET IMAGE OF A ROTATABLE MASK

[75] Inventors: John K. Shimmick, Redwood City; William B. Telfair, San Jose; Charles R. Munnerlyn, Sunnyvale; Herrmann J. Glockler, Cupertino, all of Calif.

[73] Assignee: VISX Incorporated, Santa Clara, Calif.

[21] Appl. No.: 328,937

[22] Filed: Oct. 25, 1994

Related U.S. Application Data

[63] Continuation of Ser. No. 58,600, May 7, 1993, abandoned.

[51] Int. Cl.$^6$ ............................ A61F 9/00; A61N 5/06; A61B 3/10
[52] U.S. Cl. ................................................. 606/4; 606/5
[58] Field of Search ...................... 606/4, 5, 6; 351/212, 351/227, 241; 219/121 LA

[56] References Cited

U.S. PATENT DOCUMENTS

| | | |
|---|---|---|
| 4,665,913 | 7/1987 | L'Esperance, Jr. . |
| 4,669,466 | 6/1987 | L'Esperance . |
| 4,729,372 | 3/1988 | L'Esperance, Jr. ........................ 606/5 |
| 4,732,148 | 3/1988 | L'Esperance, Jr. . |
| 4,770,172 | 9/1988 | L'Esperance, Jr. . |
| 4,773,414 | 9/1988 | L'Esperance, Jr. . |
| 4,798,204 | 1/1989 | L'Experance, Jr. ........................ 606/5 |
| 4,901,718 | 2/1990 | Bille et al. ................................ 606/4 |
| 4,907,586 | 3/1990 | Bille et al. ................................ 606/5 |
| 4,911,711 | 3/1990 | Telfair et al. . |
| 5,090,798 | 2/1992 | Kohayakawa ............................. 606/5 |
| 5,163,934 | 11/1992 | Munnerlyn ................................ 606/5 |
| 5,219,344 | 6/1993 | Yoder, Jr. ................................. 606/5 |
| 5,284,477 | 2/1994 | Hanna et al. . |
| 5,342,351 | 8/1994 | Blaha et al. .............................. 606/5 |

FOREIGN PATENT DOCUMENTS 0296982  12/1988  European Pat. Off. .......... A61F 9/00

*Primary Examiner*—Stephen C. Pellegrino
*Assistant Examiner*—Sonya Harris-Ogugua
*Attorney, Agent, or Firm*—Graham & James

[57] ABSTRACT

An ophthalmological surgery system and method for performing ablative photodecomposition of the corneal surface by offset image scanning. A mask having opaque and transparent portions corresponding to a desired type of correction, such as a hyperopic correction, intercepts a laser beam to provide a profiled beam. The mask is mounted for rotation about an axis and the image of the mask is offset from an intended center of rotation corresponding to an ablation center by an imaging lens which is radially offset from the center of rotation. The mask and lens rotate in unison to scan the image over the desired portion of the corneal surface. The invention enables wide area treatment with a laser having a narrower beam and makes optional the use of rotating mirrors and prisms.

20 Claims, 3 Drawing Sheets

METHOD AND SYSTEM FOR LASER TREATMENT OF REFRACTIVE ERROR USING AN OFFSET IMAGE OF A ROTATABLE MASK

This invention was made with Government support under Grant No. 2R44EY09491-01 awarded by Department of Health and Human Services. The Government has certain rights in the invention.

This is a continuation of application Ser. No. 08/058,600 filed May, 7, 1993, now abandoned.

BACKGROUND OF THE INVENTION

This invention relates to ophthalmological surgery techniques which employ a laser to effect ablative photodecomposition of the anterior surface of the cornea in order to correct vision defects.

Ultraviolet laser based systems and methods are known for enabling ophthalmological surgery on the surface of the cornea in order to correct vision defects by the technique known as ablative photodecomposition. In such systems and methods, the irradiated flux density and exposure time of the cornea to the ultraviolet laser radiation are so controlled as to provide a surface sculpting of the cornea to achieve a desired ultimate surface change in the cornea, all in order to correct an optical defect. Such systems and methods are disclosed in the following U.S. patents and patent applications, the disclosures of which are hereby incorporated by reference: U.S. Pat. No. 4,665,913 issued May 19, 1987 for "METHOD FOR OPHTHALMOLOGICAL SURGERY"; U.S. Pat. No. 4,669,466 issued Jun. 2, 1987 for "METHOD AND APPARATUS FOR ANALYSIS AND CORRECTION OF ABNORMAL REFRACTIVE ERRORS OF THE EYE"; U.S. Pat. No. 4,732,148 issued Mar. 22, 1988 for "METHOD FOR PERFORMING OPHTHALMIC LASER SURGERY"; U.S. Pat. No. 4,770,172 issued Sep. 13, 1988 for "METHOD OF LASER-SCULPTURE OF THE OPTICALLY USED PORTION OF THE CORNEA"; U.S. Pat. No. 4,773,414 issued Sep. 27, 1988 for "METHOD OF LASER-SCULPTURE OF THE OPTICALLY USED PORTION OF THE CORNEA"; U.S. patent application Ser. No. 109,812 filed Oct. 16, 1987 for "LASER SURGERY METHOD AND APPARATUS"; and U.S. Pat. No. 5,163,934 issued Nov. 17, 1992 for "PHOTOREFRACTIVE KERATECTOMY".

In the above-cited U.S. Pat. No. 4,665,913 several different techniques are described which are designed to effect corrections for specific types of optical errors in the eye. For example, a myopic condition is corrected by laser sculpting the anterior corneal surface to reduce the curvature. In addition, an astigmatic condition, which is typically characterized by a cylindrical component of curvature departing from the otherwise generally spherical curvature of the surface of the cornea, is corrected by effecting cylindrical ablation about the axis of cylindrical curvature of the eye. Further, a hyperopic condition is corrected by laser sculpting the corneal surface to increase the curvature.

In a typical laser surgical procedure, the region of the anterior corneal surface to be ablated in order to effect the optical correction is designated the optical zone. Depending on the nature of the desired optical correction, this zone may or may not be centered on the center of the pupil or on the apex of the anterior corneal surface.

The technique for increasing the curvature of the corneal surface for hyperopia error correction involves selectively varying the area of the cornea exposed to the laser beam radiation to produce an essentially spherical surface profile of increased curvature. This selective variation of the irradiated area may be accomplished in a variety of ways. For example, U.S. Pat. No. 4,665,913 cited above discloses the technique of scanning the region of the corneal surface to be ablated with a laser beam having a relatively small cross-sectional area (compared to the optical zone to be ablated) in such a manner that the depth of penetration increases with distance from the intended center of ablation. This is achieved by scanning the beam more times over the deeper regions than the shallow regions. As pointed out in U.S. Pat. No. 5,163,934, such ablations tend to be rougher than area ablations. The result is a new substantially spherical profile for the anterior corneal surface with maximum depth of cut at the extreme outer boundary of the optical zone. Another technique disclosed in the above-cited U.S. Pat. No. 4,732, 148 employs a rotatable mask having a plurality of elliptical annular apertures which are progressively inserted into the laser beam path to provide progressive shaping of the laser beam in order to achieve the desired profile.

One of the major difficulties encountered in the application of laser surgery techniques to effect hyperopic refractive error corrections lies in the nature of the boundary between the optical zone and the untreated area. Since the anterior surface of the cornea is sculpted during the process to have an increased curvature, the maximum depth of cut necessarily occurs at the outer boundary of the optical zone. The generally annular region between this outer boundary and the adjacent untreated anterior surface portion of the cornea typically exhibits steep walls after the completion of the photoablation procedure. After the surgery the tendency of the eye is to eliminate these steep walls by stimulated healing response involving concurrent epithelial cell growth and stromal remodelling by the deposition of collagen, which results in corneal smoothing by filling in tissue in the steep walled region. This natural healing response acts to eliminate the discontinuity, resulting in a buildup of tissue in the steep walled region and over the outer portion of the optical zone. This natural phenomenon, sometimes termed the "hyperopic shift" in phototherapeutic keratectomy, causes a lack of precision for a given surgical procedure and diminished predictability, which tend to counteract the beneficial effects of the refractive correction procedure and thereby reduce the desirability of the procedure to the prospective patient.

Efforts have been made in the past to laser sculpt a transition zone to provide a more gradual sloping of the walls and to eliminate the sharp discontinuity between the outer edge of the optical zone and the edge of the untreated area. Efforts have included the use of a beam rotation or scanning mechanism operated by a computer to provide programmed ablation of the transition zone to achieve a sigmoidal or other profile. While somewhat effective, this technique suffers from the disadvantage of typically requiring additional optical elements (such as a rotatable off-axis mirror or revolving prism having suitable optical properties) which adds complexity to the delivery system optics commonly found in laser sculpting ophthalmological surgical systems. One specific technique, which is disclosed in published European Patent Application No. 0 296 982 published Dec. 28, 1988, employs a rotatable mask having one or more profiling apertures whose shape is designed to provide a smoother profile in the transition zone in the course of performing a specific ablation procedure. This reference also teaches the use of a rotating prism aligned along the beam axis in combination with a translatable platform bearing a focusing lens in order to both translate and rotate the aperture image along the anterior corneal surface. This technique, while considered effective for some purposes, requires a relatively complicated optical delivery system in order to provide the desired profiling. In addition, the use of mirrors and prisms in delivery system optics in laser surgery systems suffers from certain disadvantages. In particular, the addition of prisms decreases the total energy transmission of the system. Further, the reflectance of dielectric mirrors used in certain systems varies with reflectance angle, which can dynamically alter the irradiance delivered to the cornea while displacing the beam image over the cornea.

Another difficulty encountered in the application of laser surgery techniques to effect hyperopic refractive error corrections lies in the requirement for relatively large transition zones outside the optical zone. In particular, while the intended optical zone is typically on the order of about 5 mm in diameter, the outer limit of the transition zone can be as large as 10 mm in diameter. If the rotating mask arrangement described above is used to effect the ablation in both the optical zone and the transition zone, the beam diameter must be commensurate in size with the largest aperture outer diameter (i.e., at least about 10 mm). In general, the larger the beam diameter the less uniform the energy density across the beam and the less reliable the photoablation process. Further, the increased beam area requires a laser beam of substantially greater energy, which necessitates a more expensive laser. Also, the increased energy flowing through the optical components causes optical deterioration at a faster rate, thereby increasing maintenance and replacement costs.

SUMMARY OF THE INVENTION

The invention comprises a method and system for performing ablative photodecomposition of the corneal surface which is capable of providing relatively smooth transition zones along with accurate sculpting of the anterior or other corneal surface to effect desired hyperopic or other types of refractive corrections requiring relatively large area coverage, which may use, but does not require, rotating mirrors or prisms, and which can be relatively simple to install in existing optical delivery systems.

From a system standpoint, the invention includes a laser beam generating device for producing a beam of radiation along a path, a beam profiling mask arranged along the path for shaping the beam to a desired profile and means for translationally displacing the profiled beam from the path to an offset position and for varying the angular position of the offset beam about a center of rotation corresponding to a desired ablation center. The mask has predetermined opaque and transparent regions corresponding to a desired type of refractive correction to the surface of the cornea and the means for varying the angular position of the offset beam preferably includes a lens and means for rotating the lens and the mask about the center of rotation.

From a method standpoint, the invention includes the step of directing a laser beam along a beam path, profiling the beam with a mask to produce a profiled beam, displacing the profiled beam from the path, and varying the angular position of the profiled beam to cause the beam to describe a path about a center of rotation corresponding to a desired ablation center. The mask has opaque and transparent regions corresponding to a desired type of refractive correction and the step of varying the angular position of the profiled beam includes the step of rotating the image of the profiled beam and the mask about the center of rotation.

When used to effect a predetermined hyperopic refractive correction, the method comprises the step of directing a laser beam along a beam path, selectively irradiating a corneal surface of the eye to ablate the appropriate contour to produce the hyperopic refractive correction by profiling the beam with a mask having opaque and transparent regions corresponding to the appropriate contour, displacing the profiled beam from a center of rotation corresponding to an intended center of ablation and varying the angular position of the profiled beam by rotating the image of the profiled beam and the mask about the center of rotation.

The system and method can be incorporated into existing laser surgery systems having an imaging lens and an aperture platform which is rotatably mounted by mounting the mask on the aperture platform and modifying the existing imaging lens mounting mechanism to provide a predetermined offset for the profiled beam from the intended center of rotation and to enable the lens to be rotated along with the mask. The invention is capable of providing wider area beam coverage of the corneal surface with a laser having a conventional beam size, thereby eliminating any need for a larger beam laser and providing wider area coverage with lower energy requirements than many known devices. In addition, the invention avoids the need for rotating mirrors and prisms so that the adverse effects of these elements can be eliminated.

For a fuller understanding of the nature and advantages of the invention, reference should be had to the ensuing detailed description taken in conjunction with the accompanying drawings.

DESCRIPTION OF THE PREFERRED EMBODIMENTS

Figure 1:
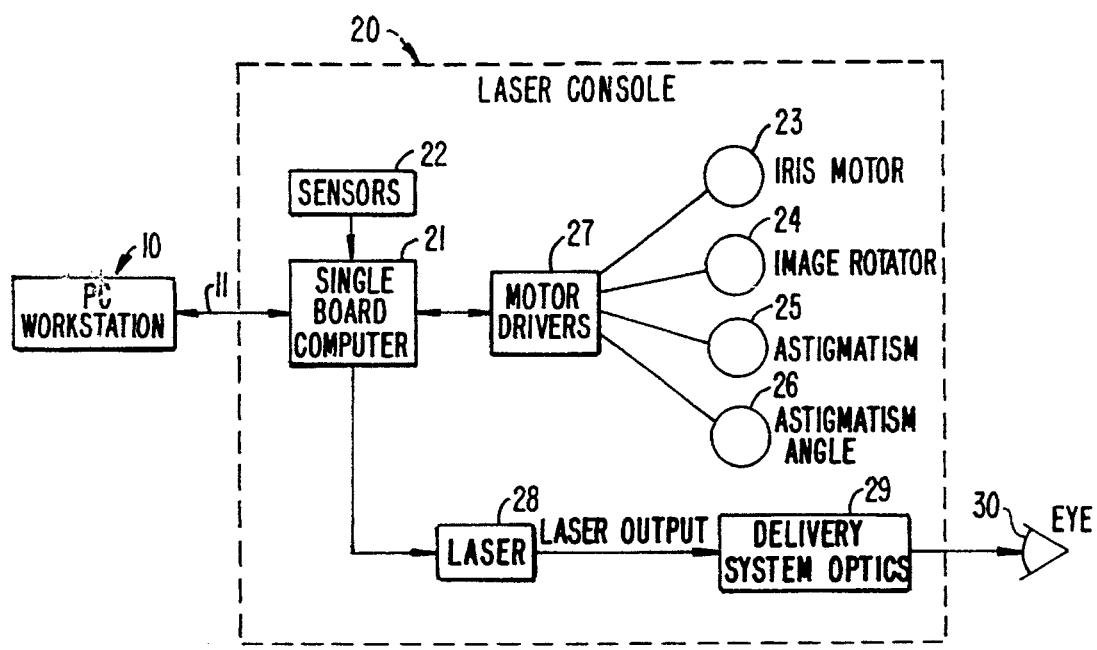
FIG. 1 is a block diagram of an ophthalmological surgery system for incorporating the invention.

Turning now to the drawings, FIG. 1 illustrates a block diagram of an ophthalmological surgery system for incorporating the invention. As seen in this Fig., a personal computer (PC) work station 10 is coupled to a single board computer 21 of a laser surgery unit 20 by means of a first bus connection 11. PC work station 10 and the subcomponents of laser surgery unit 20 are known components and preferably comprise the elements of the VISX TWENTY/TWENTY EXCIMER LASER SYSTEM available from Visx, Incorporated of Santa Clara, Calif. Thus, the laser surgery system 20 includes a plurality of sensors generally designated with reference numeral 22 which produce feedback signals from the movable mechanical and optical components in the laser optical system, such as the elements driven by an iris motor 23, an image rotator 24, an astigmatism motor 25 and an astigmatism angle motor 26. The feedback signals from sensors 22 are provided via appropriate signal conductors to the single board computer 21, which is preferably an STD bus compatible single board computer using a type 8031 microprocessor. The single board computer 21 controls the operation of the motor drivers generally designated with reference numeral 27 for operating the elements 23–26. In addition, single board computer 21 controls the operation of the Excimer laser 28, which is preferably an argon-fluorine laser with a 193 nanometer wavelength output designed to provide feedback stabilized fluence of 160 mJoules per $cm^2$ at the cornea of the patient's eye 30 via the delivery system optics generally designated with reference numeral 29 and shown in FIG. 5. Other ancillary components of the laser surgery system 20 which are not necessary to an understanding of the invention, such as a high resolution microscope, a video monitor for the microscope, a patient eye retention system, and an ablation effluent evacuator/filter, as well as the gas delivery system, have been omitted to avoid prolixity. Similarly, the keyboard, display, and conventional PC subsystem components (e.g., flexible and hard disk drives, memory boards and the like) have been omitted from the depiction of the PC work station 10.

Figure 2:
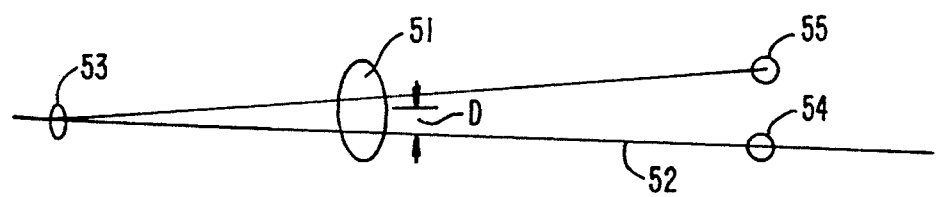
FIG. 2 is a schematic diagram illustrating the offset lens principle.
Figure 3:
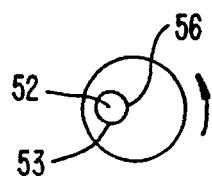
FIG. 3 is a schematic diagram illustrating the lens offset viewed along the axis of rotation.

The system of FIG. 1 is used according to the invention to effect hyperopic and other error corrections to the anterior or other surface of the cornea, and to provide a smooth transition zone between the outer edge of the optical zone and the untreated surface of the cornea. The principle of the invention is illustrated in FIG. 2. As seen in this Fig., an imaging lens 51 is laterally offset from an image axis 52 by a predetermined radial distance D. Lens 51 preferably comprises the existing imaging lens found in the delivery system optics 29 of the FIG. 1 system (see also FIG. 5, described below). Axis 52 is the axis corresponding to the center of rotation of lens 51. Lens 51 is displaced by translating the lens in a radial direction off the axis 52 (which may or may not correspond to the laser beam axis), which displaces the image of aperture 53 in a related manner from an initial position 54 to an offset position 55. By also rotating lens 51 about the axis 52 in an eccentric fashion, as illustrated in FIG. 3, the displaced image of aperture 53 can be scanned about axis 52 along a preselected path, which in the embodiment described below is an annular path about the axis 52. In FIG. 3, the path described by the lens center is designated with reference numeral 56. By using a rotatable mask in combination with the off axis translation of lens 51 and eccentric rotation of lens 51 about axis 52, various types of large area ablation corrections can be effected, including hyperopic error corrections, and other vision error corrections, along with simultaneous edge contouring to form a smooth transition zone.

Figure 4:
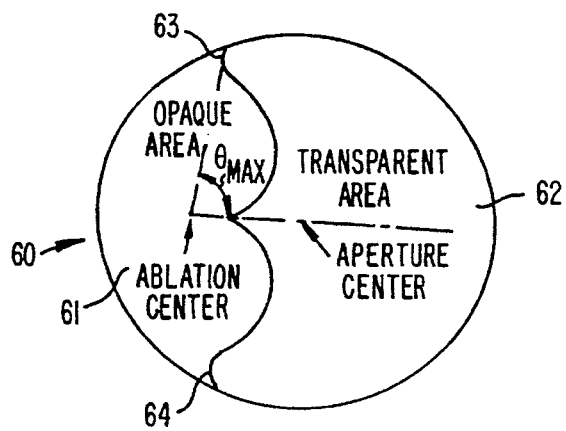
FIG. 4 is a schematic view of an aperture mask for use in hyperopia correction.

FIG. 4 illustrates an embodiment of a mask 60 used to effect hyperopic corrections when used in combination with the imaging lens 51. The mask shown in FIG. 4 has an opaque area 61 and a transparent area 62. The boundary between the two areas has the required mathematical shape to ablate the appropriate surface contour in the cornea to effect a predetermined hyperopic error correction. In addition, the boundary shape can also incorporate a compensation factor to accommodate for variations in the energy profile of the laser beam. Portions 63, 64 of the boundary are shaped to provide a smooth transition zone between the outer edge of the intended optical zone of the corneal surface and the untreated area of the corneal surface. By changing this shape, different transition zone curvatures can be obtained. Further, the portion of mask 60 comprising the center of ablation can be shaped so that the corneal surface is left unablated at the center and over a limited region extending a predetermined distance radially outwardly, typically on the order of one-half to one mm. The image of the mask is initially offset with the lens 51 so that the intended center of the ablation of the mask is imaged over the intended ablation center on the cornea. Thereafter, lens 51 is synchronously rotated with mask 60 over an angular range of 360° or multiples of 360° while pulsing laser 28 to simultaneously effect hyperopic correction with edge contouring to provide a gentle transition zone extending outwardly to the untreated corneal surface.

To align the mask to the desired offset position, the optical center of lens 51 is first determined using a mask with a pinpoint aperture, and rotating lens 51 while adjusting the lateral position of a reference axis until the image of the aperture is essentially invariant over a 360° rotation of lens 51. Thereafter, the pinhole alignment mask is removed and replaced by mask 60, and the ablation center of mask 60 is aligned to the former position of the aperture center image by radially displacing lens 51. Thus aligned, the image of the profiled beam passing through mask 60 can be rotated about the ablation center in the eccentric manner described above.

Figure 5:
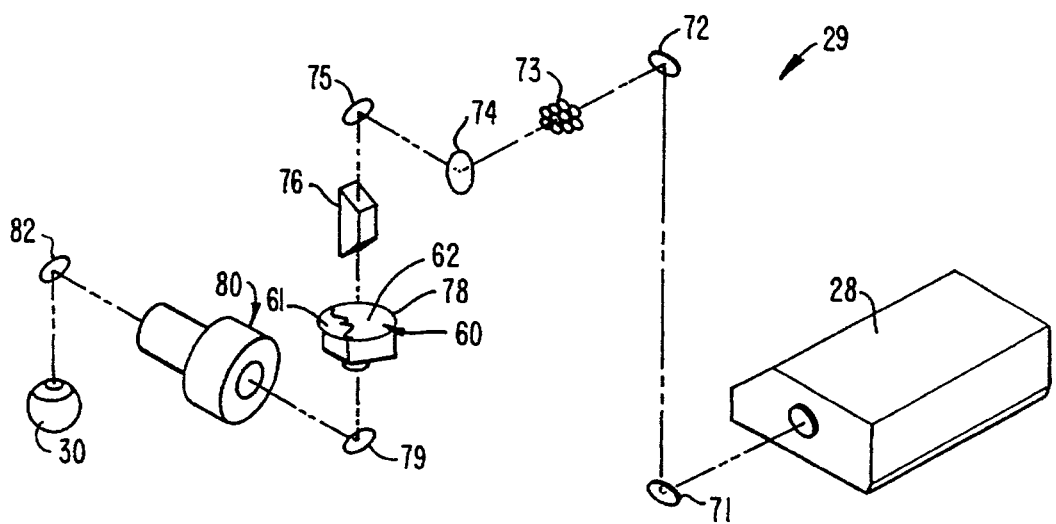
FIG. 5 is a schematic diagram illustrating the delivery system optics.

FIG. 5 is a schematic view of the delivery system optics in the preferred embodiment. As seen in this Fig. the beam from laser 28 is reflected by a first mirror 71 and a second mirror 72, and enters a spatial integrator 73, where the beam is modified in cross-section. The modified beam exiting from spatial integrator 73 is reflected by mirrors 74 and 75 and passed through a dove prism 76 to the mask rotation mechanism 78 on which the mask 60 is mounted. The profiled beam exiting from the mechanism 78 is reflected by a mirror 79 and enters the image offset control unit 80 which contains imaging lens 51. Unit 80 is illustrated schematically in FIGS. 6 and 7. The offset profiled image exiting from unit 80 is reflected from a mirror 82 onto the patient's eye.

Figure 6:
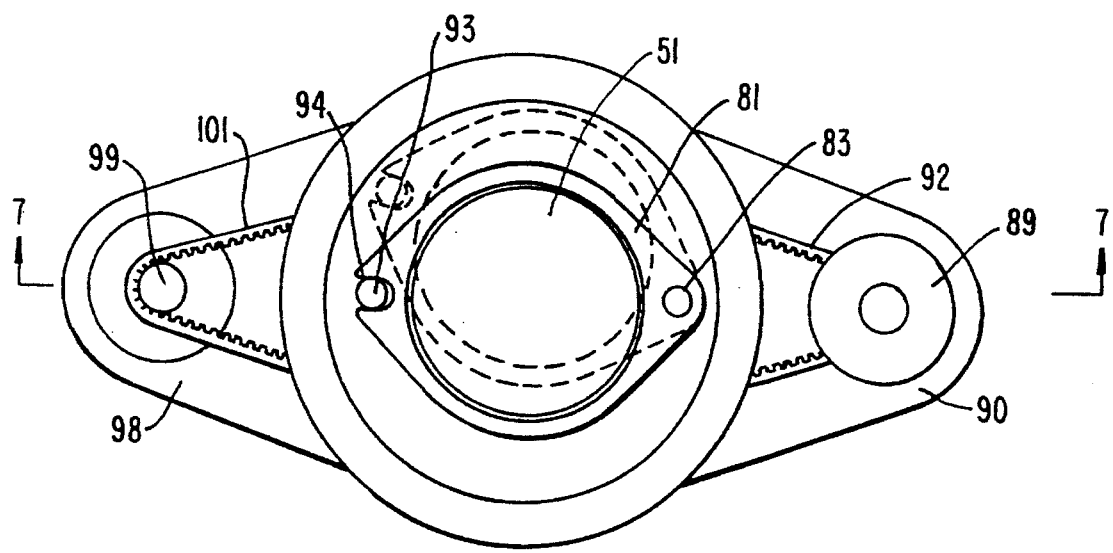
FIG. 6 is a top plan view of the image offset control unit of the invention, with the top annular portion removed.
Figure 7:
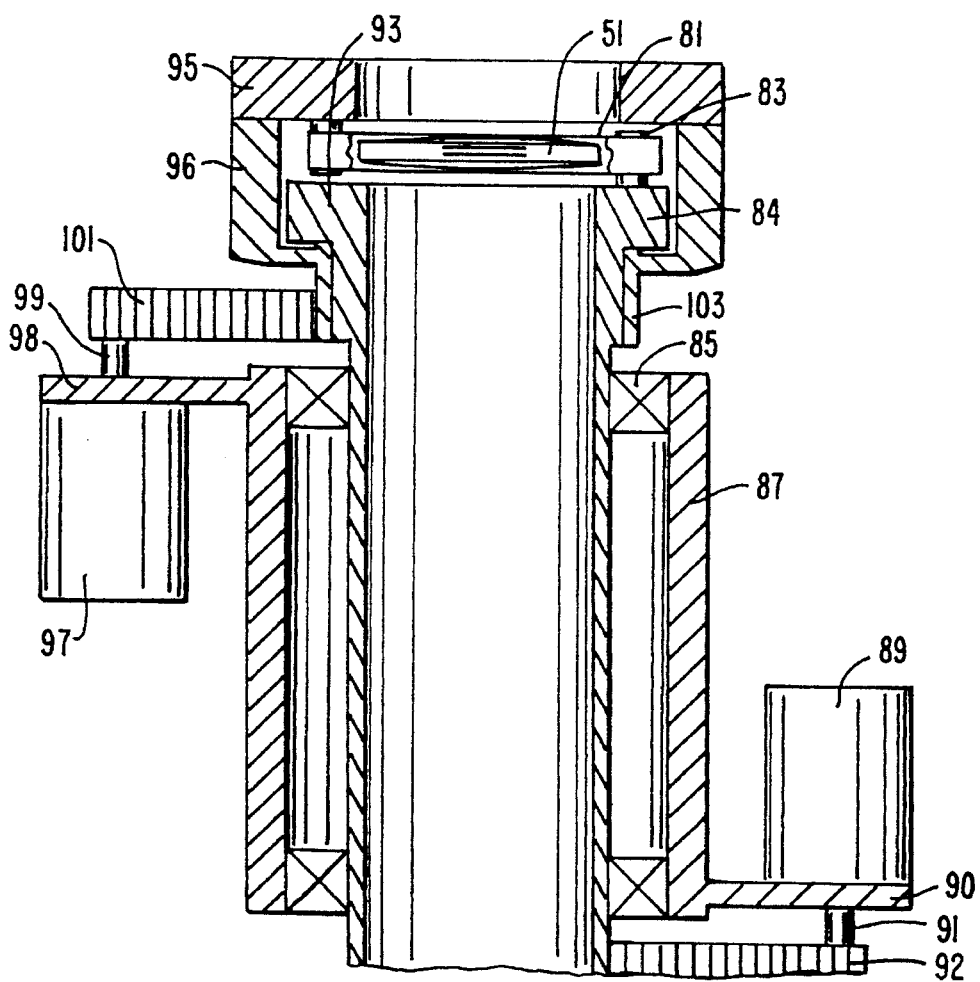
FIG. 7 is a side sectional view taken along lines 7—7 of FIG. 6.

FIGS. 6 and 7 illustrate the image offset control unit 80. As seen in these Figs., imaging lens 51 is contained in a fixture 81, which is mounted for pivotal motion about a first pivot post 83. Post 83 is carried by a first mounting member 84, which in turn is mounted by means of bearings 85 (or other suitable mounting mechanisms) for rotation about the longitudinal axis of member 84. Bearings 85 are mounted in the internal recess of a fixture housing 87. A first drive motor 89 is mounted on a flange portion 90 of housing 87 and has an output shaft 91 for driving a first drive belt 92 which is coupled to the lower portion of member 84. A second pivot post 93 is received in a second pivot aperture 94 formed in fixture 81. Second post 93 is secured to an annular upper portion 95 of a second rotatable member 96. A second drive motor 97 is mounted on a second flange portion 98 of fixture housing 87 and has an output shaft 99 for driving a second drive belt 101. Second drive belt 101 is arranged in driving engagement with the lower collar portion 103 of member 96.

In operation, when member 84 is driven by motor 89 and belt 92, the lens housing 81 pivots about post 93. Similarly, when outer member 96 is driven by motor 97 and belt 101, housing 81 is pivoted about post 83. This latter motion is suggested in FIG. 6, in which two different positions of the housing 81 are illustrated: one in full lines and the other in broken lines. By operating motors 89, 97 simultaneously, compound motion of the housing 81 in a plane about both pivot posts 83, 93 can be effected so that both translational and rotational motion can be imparted to the lens 51. Motors 89 and 97 are driven by the on-board computer 21, which is in turn driven by the p.c. workstation 10. By properly programming workstation 10, the desired motion can be imparted to imaging lens 51 and mask rotation mechanism 78 in order to scan the aperture image over the desired ablation region of the corneal surface.

Referring back to FIG. 4, in order to determine the desired motion for the aperture image scanning, the depth of the required ablation is first selected. Next, the number of pulses required to effect ablation to that depth is determined from the equation:

$$n = t\pi/dx\theta_{max}$$

where t is the desired ablation depth at the edge of the optical zone, d is the ablation depth per laser pulse (or a scaling factor thereof) and θ max is the angle subtended between a line passing through the ablation center and the aperture center and a line passing from the ablation center to the point on the mask profile corresponding to the outer edge of the desired optical zone. Once the number of pulses has been determined, the angle of rotation between laser pulses can be chosen taking into consideration the length of time required by the mechanical elements in the system to reposition the lens 51 and the mask 60 (i.e., the minimum time), the amount of successive image overlap which can be tolerated, and the size of the optical zone desired.

The invention offers the advantage of relatively wide area coverage without requiring a laser beam of size approximately equal to the treatment area. As a consequence, for hyperopic error corrections the transition zone can be fully formed using a controlled laser beam having a beam area substantially smaller than those required in prior art systems. This is highly advantageous since it requires substantially less energy than a larger beam generating laser, and avoids premature failure of optical components which are subject to deterioration due to high energy levels. The laser beam size should be large enough to span from the center of rotation to the outer boundary of the desired transition zone. For most human eyes, the largest treatment area is approximately 10 mm. Consequently, a laser having a beam diameter of about 5 mm will provide satisfactory ablations according to the invention. In the preferred embodiment the laser has a beam with a 6 mm maximum width. Further, the invention can be implemented in existing laser surgery systems by merely modifying the delivery system optics to enable the imaging lens 51 to be offset from the beam axis by selected amounts and to rotate with the mask 60. The design and construction of such modifications will be readily apparent to those of ordinary skill in the art of optomechanical design. Because the invention obviates the need for rotating mirrors and prisms, the difficulties noted above encountered with the use of such optical elements can be completely eliminated, when desired.

While the invention has been described above with reference to ablation of the anterior corneal surface, other portions of the cornea may also be treated using the invention. For example, the epithelium may be mechanically removed by scraping, as is typically done in photorefractive keratectomy, and the exposed surface may be ablated. Further, the invention can also be used for laser keratomileusis of corneal lamella removed from the cornea. This procedure is described in U.S. Pat. No. 4,903,695 issued Feb. 27, 1990 for "Method and Apparatus For Performing A Keratomileusis Or The Like Operation". In applying the invention to this procedure, a flap of corneal tissue is physically removed from the cornea, the size of the removed portion typically lying in the range from about 8 to 10 mm wide and a variable thickness up to 400 microns. This flap of tissue is typically removed using a microkeratome. Next, the flap is placed in a suitable fixture - typically an element having a concave surface - with the anterior surface face down. Thereafter, the required ablation is performed on the reverse exposed surface of the flap, after which the ablated flap is repositioned on the cornea and reattached by suturing. Alternatively, after the flap is removed from the cornea, the exposed stromal tissue of the eye can be ablated according to the invention, after which the flap is re-attached over the freshly ablated stromal tissue.

While the above provides a full and complete disclosure of the preferred embodiments of the invention, various modifications, alternate constructions and equivalents may be employed as desired. For example, while the invention has been disclosed and described with respect to a mask 60 suitable for use in performing hyperopic corrections, mask profiles designed to achieve other types of corrections may be employed, as desired. Also, while the invention has been disclosed and described with reference to an imaging lens offset mechanism which is both rotatable and translatable by selected amounts, a simpler mechanism providing a fixed amount of offset for the image of the mask may be employed, as desired. Therefore, the above description and illustrations should not be construed as limiting the invention, which is defined by the appended claims.

What is claimed is:

1. An ophthalmological surgery system for performing ablative photodecomposition of a corneal surface, said system comprising:

a laser beam generating device for producing a beam of radiation along a path;

a beam profiling mask arranged along said path, said mask having opaque and transparent regions for shaping the beam to a desired profile;

means for rotating said mask so as to rotate said profile; and means for translationally displacing the profiled beam from the path to a position offset from a center of rotation corresponding to a desired center of ablation and for varying the position of the offset profiled beam about a center of rotation corresponding to a desired ablation center.

2. The invention of claim 1 wherein said opaque and transparent regions of said mask correspond to a desired type of correction to the surface of the cornea.

3. The invention of claim 1 further including laser control means for generating a pulsed beam.

4. The invention of claim 3 wherein said control means includes means for synchronizing the generation of a beam pulse with said rotating means so that said mask and lens are properly positioned when the laser beam is pulsed.

5. The invention of claim 1 wherein said displacing means comprises an imaging lens.

6. The invention of claim 5 wherein said displacing means further includes means for rotating said lens about the center of rotation.

7. A method of performing selective ablation of a corneal surface of an eye to effect a predetermined vision correction having a desired geometrical center, said method comprising the steps of:

(a) directing a laser beam along a beam path;

(b) profiling said beam with a mask having opaque and transparent regions to produce a profiled beam having an image;

(c) rotating said mask so as to rotate said image;

(d) displacing said profiled beam from said path to a position offset from a center of rotation corresponding to said geometrical center; and (e) rotating the image of the profiled beam about the center of rotation to cause said profiled beam to describe a path about the center of rotation corresponding to said desired geometrical center.

8. The method of claim 7 wherein the opaque and transparent regions of the mask correspond to the predetermined vision correction to the surface of the cornea.

9. The method of claim 8 wherein said center of rotation corresponds to said beam path.

10. The method of claim 7 wherein said step (a) of directing includes the step of operating the laser beam in a pulsed manner; and wherein said step (d) of rotating includes the step of repositioning the image when the laser beam is off.

11. The method of claim 7 wherein said step (d) of rotating is performed over an integral multiple of revolutions about the center of rotation.

12. The method of claim 7 wherein the corneal surface is an anterior corneal surface.

13. The method of claim 7 wherein the corneal surface is a surface of an cornea exposed by removing the epithelium.

14. The method of claim 7 wherein the corneal surface is a posterior surface of a section cut from the cornea.

15. A method of performing selective ablation of a corneal surface of an eye to effect a predetermined hyperopic type of refractive correction, the ablation having an intended center, said method comprising the steps of:

(a) directing a laser beam along a beam path; and (b) selectively irradiating a corneal surface of the eye to produce said hyperopic type of refractive correction by:
  (i) profiling said beam with a mask having opaque and transparent regions corresponding to said hyperopic type of refractive correction to produce a profiled beam having an image;
  (ii) rotating said mask so as to rotate the image;
  (iii) displacing the profiled beam from said path to a position offset from a center of rotation corresponding to the center of ablation; and
  (iv) varying the angular position of the profiled beam by rotating the image of the profiled beam about the center of rotation.

16. The method of claim 15 wherein said step (iii) of displacing is performed by positioning an imaging lens in the path of the profiled beam and displacing the imaging lens with respect to the center of rotation.

17. The method of claim 15 wherein said step (iii) of displacing is performed with an imaging lens.

18. The method of claim 15 wherein the corneal surface is the anterior corneal surface.

19. The method of claim 15 wherein the corneal surface is a surface of an cornea exposed by removing an epithelium.

20. The method of claim 15 wherein the corneal surface is a posterior surface of a section cut from the cornea.

* * * * *